United States Patent [19]

Moore et al.

[11] 3,937,734

[45] Feb. 10, 1976

[54] PROCESS FOR PRODUCING DECACHLOROOCTAHYDRO-1,3,4-METHENO-2H-CYCLOBUTA-(C,D)-PENTALEN-2-ONE

[75] Inventors: William Percy Moore, Hopewell; Virgil Anton Hundtofte, Chester, both of Va.

[73] Assignee: Allied Chemical Corporation, New York, N.Y.

[22] Filed: Jan. 3, 1975

[21] Appl. No.: 538,493

[52] U.S. Cl. .......................... 260/586 R; 260/586 G
[51] Int. Cl.² ........................................ C07C 45/00
[58] Field of Search ..................... 260/586 R, 586 G

[56] References Cited
UNITED STATES PATENTS

| | | | |
|---|---|---|---|
| 3,333,003 | 7/1967 | Du Bois | 260/586 R |
| R24,435 | 2/1958 | Gilbert et al. | 260/586 G |

*Primary Examiner*—Norman Morgenstern
*Attorney, Agent, or Firm*—Fred L. Kelly

[57] ABSTRACT

A process for producing a relatively high yield of pure decachlorooctahydro-1,3,4-metheno-2H-cyclobuta(c,d)-pentalen-2-one ($C_{10}Cl_{10}O$) having high purity. In particular, the $C_{10}Cl_{10}O$ is produced without formation of toxic waste streams by condensing two molecules of hexachlorocyclopentadiene with the aid of excess sulfur trioxide in the presence of a catalytic quantity of an antimony compound at a temperature within the range 95°–120°C. and at superatmospheric pressure to form a reaction product and hydrolyzing the reaction product. The hydrolysis is carried out in aqueous alkaline solution having a pH of at least about 9, and at a temperature within the range 85°–115°C. The resulting hydrolysis mixture is acidified to a pH 5-6, preferably 5.4–5.6, to precipitate crystalline product which is filtered, washed and dried. The product $C_{10}Cl_{10}O$ is an effective insecticide with low toxicity to animals and human beings at prescribed dosages.

10 Claims, No Drawings

PROCESS FOR PRODUCING DECACHLOROOCTAHYDRO-1,3,4-METHENO-2H-CYCLOBUTA-(c,d)-PENTALEN-2-ONE

BACKGROUND OF THE INVENTION

This invention relates to a process for producing decachlorooctahydro-1,3,4-metheno-2H-cyclobuta(c,d)-pentalen-2-one, hereinafter referred to as $C_{10}Cl_{10}O$. $C_{10}Cl_{10}O$ is a complex chlorinated polycyclic ketone having a molecular weight of 490.68. It is believed to be most accurately represented by the following cage structural formula:

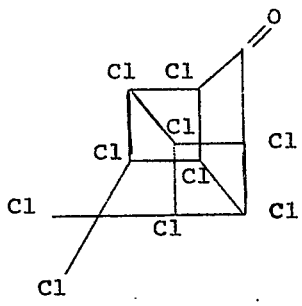

In U.S. Reissue Pat. No. 24,435 of Everett E. Gilbert and Silvio L. Giolito granted Feb. 25, 1958, (original U.S. Pat. No. 2,616,928 dated Nov. 4, 1952) there is described a process for preparing a biocidally active $C_{10}Cl_{10}O$ ketone and its hydrates by reacting hexachlorocyclopentadiene and sulfur trioxide at temperatures in the range of about 35°C. to about 70°C. to form a reaction product thereof and hydrolyzing the resulting reaction product.

The above ketone product has proved to be of outstanding value in numerous biocidal applications, particularly in the control of ants, roaches and other resistant pests.

The original preparative process of the above reissue patent, while quite satisfactory in most respects often resulted in low yields of ketone product or required long reaction times to produce desired yields, and such long reaction times tended to produce a degraded product, particularly with respect to color and the presence of impurities including inorganic (methanol insoluble) impurities.

More recently, it has been suggested in U.S. Pat. No. 3,333,003 of R. J. DuBois, granted July 25, 1967, to produce $C_{10}Cl_{10}O$ by reacting hexachlorocyclopentadiene and sulfur trioxide at temperatures between 35°C. and 90°C. using an antimony compound as catalyst, and hydrolyzing the reaction product. However, in commercial use of this prior process, serious problems were encountered because of the formation of a toxic aqueous waste stream which tended to pollute the environment.

Under this prior process, the yield of the $C_{10}Cl_{10}O$, in particular the purified $C_{10}Cl_{10}O$, generally was in the range 80-90%; however, in order to obtain a yield of about 90% a reaction time of 2-4 hours or more was necessary. Furthermore, the $C_{10}Cl_{10}O$ product was relatively impure. Obviously, it is desirable to prepare a product of high assay, which is generally indicated by infrared assay. Methanol insolubles indicate presence of inorganic impurities.

Accordingly, it is an object of this invention to produce $C_{10}Cl_{10}O$ by a process which results in a high yield.

It is another object of this invention to produce $C_{10}Cl_{10}O$ in high yield without formation of a toxic aqueous waste stream.

It is another object of this invention to produce $C_{10}Cl_{10}O$ of good quality and high yield.

It is an additional object of this invention to produce $C_{10}Cl_{10}O$ at relatively high temperatures whereby reaction time is substantially decreased over prior art processes.

SUMMARY OF THE INVENTION

In accordance with the present invention, decachlorooctahydro-1,3,4-metheno-2H-cyclobuta (c,d)-pentalen-2-one is produced in at least 95% yield. Briefly stated, the instant process comprises:

a. reacting hexachlorocyclopentadiene and sulfur trioxide at a temperature between about 95°C. and about 120°C., at a pressure of between 50 p.s.i.g. and 300 p.s.i.g., in the presence of a catalytic quantity of an antimony compound, preferably selected from the group consisting of trivalent and pentavalent antimony halides, oxides and oxy acids, the mole ratio of sulfur trioxide to hexachlorocyclopentadiene being between about 1.5 and 2, to form a reaction product thereof;

b. hydrolyzing the reaction product from step (a) in at least about 5 parts by weight of an aqueous solution containing dissolved caustic alkali and having a pH of at least 9, per part by weight of reaction mixture, said hydrolysis being carried out at a temperature between about 85°C. and about 115°C. for at least about 30 minutes, preferably 60 to 120 minutes;

c. acidifying the hydrolysis mixture from step (b) with a mineral acid, preferably sulfuric acid, to pH 5–6, preferably to pH 5.4–5.6;

d. digesting the acidified hydrolysis mixture at pH 5–6, preferably 5.4–5.6, at a temperature between about 85°C. and about 105°C. for at least 1 hour, preferably 1–4 hours, whereby substantially all of the decachlorooctahydro-1,3,4-metheno-2H-cyclobuta(c,d)-pentalen-2-one is precipitated as a crystalline product; and e. recovering the crystalline product from the digestion mixture.

The crystalline product can be recovered from the digestion mixture by mechanical means, as by filtration, leaving in solution the salts formed in acidifying the hydrolysis mixture. The filtered product is washed and dried for storage and use.

As brought out above, our improved process is substantially similar to the process of U.S. Pat. No. 3,333,003, particularly with respect to the addition of the antimony catalyst. Accordingly, any compound of antimony can be used which can be dispersed per se in the hexachlorocyclopentadiene reactant or after solution in water. Both the trivalent and pentavalent forms of antimony are suitable as catalysts.

Antimony compounds which are especially suitable for use as catalyst in our invention include antimony trichloride, antimony pentachloride, antimony trioxide, antimony pentoxide, antimony trifluoride and the antimonic and antimonous acids $HSbO_3$ and $HsbO_2$. Antimony pentachloride is preferred, and we find this compound especially suitable when used in the presence of a small amount of water indicating that reactions may take place to convert at least a portion of the pentachloride to hydrolysis products, possibly including one or more of $Sb_2O_5$, $SbOCl_3$ and $SbOCl$.

A small amount of water, e.g., of the order of 0.1 to 9.0% based on the weight of the antimony pentachloride is usually sufficient to promote hydrolysis and enhance the activity of this catalyst. The amount of water added can be as high as 22%.

Proportions of antimony compound effective in promoting the reaction are quite small, amounts of as little as about 0.25% or less by weight based on the weight of the hexachlorocyclopentadiene being adequate. Quantities in excess of about 1% appear to provide little if any further stimulation of the reaction. In general, amounts of catalyst between about 0.10% and about 0.5% based on the weight of hexachlorocyclopentadiene are satisfactory.

DESCRIPTION OF THE PREFERRED EMBODIMENTS

The invention will now be further described in the following specific examples which are to be regarded solely as illustrative and not as restricting the scope of the invention.

EXAMPLE 1

A charge of 9,500 pounds of hexachlorocyclopentadiene (HCP) is fed to a pressure-type reactor equipped with agitator and jacket for heating and cooling. To this charge are added with agitation 20 pounds of antimony pentachloride and 1.4 pounds of water, and the charge is heated to about 60°C. The reactor vent valves are closed, and 3,200 pounds of stabilized liquid sulfur trioxide are added over a period of about 1.5 hours. During addition of the sulfur trioxide, the temperature of the reaction mixture is maintained below about 105°C. by means of cooling water in the reactor jacket. Pressure in the reactor is about 85–115 p.s.i.g. The rate of feed of the sulfur trioxide is limited by the ability of the reactor cooling jacket to remove the heat generated in the reactor. When addition of the sulfur trioxide is complete, the reaction mixture is maintained at 95°–105°C. for 1 to 2 hours. During the first part of the reaction, the reaction mixture is dark and cloudy but it becomes a clear cherry wine color near the end of the reaction period. When the reaction mixture turns from a cherry color to a black color, the reaction is immediately stopped by cooling the reaction mixture to near ambient temperature. On cooling, pressure in the reactor drops to near atmospheric.

The adduct of HCP-$SO_3$ thus formed is fed to a hydrolysis reactor containing about 83,000 pounds of water and about 8,375 pounds of 50 weight percent aqueous sodium hydroxide at about 70°C. The hydrolysis mixture is agitated by means of circulating pumps and an air sparger. The hydrolysis reactor is equipped for cooling, and the HCP-$SO_3$ adduct is added at a rate to maintain the hydrolysis mixture at about 90°–96°C. After addition of the HCP-$SO_3$ adduct is complete, the hydrolysis mixture is agitated and maintained at about 90°–96°C. for about 90 minutes. The pH of the hydrolysis mixture is about 9.5–10.5. As soon as all solids have gone into solution, the temperature of the solution is maintained at 85°–96°C. by cooling, and the solution is acidified to pH 5.4–5.6 with about 800 pounds of concentrated (96%) sulfuric acid. After the acidification, the temperature of the mixture is maintained at 85°–96°C. for 1–4 hours to allow complete precipitation of hydrolyzed product. The precipitate is recovered by filtration using a rotary vacuum filter. The wet filter cake is washed free of inorganic salts using about 0.7–2.0 pounds of wash water per pound of filter cake. The wet cake is dried at 93°–94°C. in a rotary tray dryer. Yield of $C_{10}Cl_{10}O$, calculated as anhydrous product, is over 99% of theory based on feed of HCP. Purity of the product was over 98% based on infrared assay. Methanol insolubles was about 0.01%.

EXAMPLE 2

Concentrated sulfuric acid (95% $H_2SO_4$) is used in a conventional vent scrubber to scrub sulfur trioxide vapor or mist from the reaction vessel in Example 1. The vent scrubber is used intermittently, only when the vessel is being vented, as when the vessel is being filled with HCP. As the sulfuric acid scrubs sulfur trioxide, acid strength increases by converting the sulfur trioxide into additional sulfuric acid. When the sulfuric acid strength goes above 100%, its effectiveness as a sulfur trioxide scrubber is decreased, and the acid in the scrubber is desirably replaced with 95% $H_2SO_4$. The more concentrated acid may be utilized in the acidification step of the process.

EXAMPLE 3

The following procedure is preferably used for treatment of filtrate to be discharged as effluent from $C_{10}Cl_{10}O$ plant. The main filtrate from draining the $C_{10}Cl_{10}O$ filter cake in Example 1 and the wash water from washing this filter cake are collected together into a filtrate tank. This filtrate is then passed to a leaf filter to remove any traces of suspended $C_{10}Cl_{10}O$. The resulting effluent water contains about 1.5 ppm $C_{10}Cl_{10}O$. Preferably, the effluent water leaving the plant is further treated by filtering through a bed of charcoal (in powder, granular, or pellet form) whereby the $C_{10}Cl_{10}O$ in the effluent stream is reduced to 0.1 to 0.001 ppm.

EXAMPLE 4

A run was carried out in accordance with the procedure of Example 1 except that the sulfur trioxide was reacted with the HCP in the presence of the catalyst at temperatures between 78° and 95°C., the average reaction temperature being about 86°C. About three hours reaction time was required, as compared with 1.5 hours reaction time in Example 1. Moreover, even with this longer reaction time, the yield of $C_{10}Cl_{10}O$ was only 80% on an anhydrous basis. Infrared assay revealed a purity of about 95%, and methanol impurities amounted to about 2%. This comparative example shows the importance of maintaining an average reaction temperature above about 95°C. in accordance with the present invention.

EXAMPLE 5

A run was carried out in a manner identical to that described in Example 1 except that the amount of sulfuric acid added to the hydrolysis mixture in the acidification step was decreased, whereby the pH of the acidified mixture was about 6.2 instead of pH 5.4–5.6 as in Example 1. Surprisingly, the amount of $C_{10}Cl_{10}O$ in the filtrate during the filtration step increased to 200 ppm from 1.5 ppm in Example 1. Additional tests showed that this pH factor is very critical to economic operation of the process. Moreover, care must be taken because the pH usually increases slightly after initial acidification. Therefore, a recheck of acidity should be made prior to filtration of the product. As disclosed hereinabove, the acidity of the mixture is preferably adjusted to pH 5.4–5.6. Obviously, it is important to maintain as little $C_{10}Cl_{10}O$ as possible in the filtrate to avoid possible pollution of the environment by toxic aqueous waste streams from the process.

We claim:

1. A process for producing decachlorooctahydro-1,3,4-metheno-2H-cyclobuta(c,d)-pentalen-2-one in at least 95% yield, which comprises:
   a. reacting hexachlorocyclopentadiene and sulfur trioxide at a temperature between about 95°C. and about 120°C., at a pressure of between 50 p.s.i.g. and 300 p.s.i.g., in the presence of a catalytic quantity of an antimony compound selected from the group consisting of trivalent and pentavalent antimony halides, oxides and oxy acids, the mol ratio of sulfur trioxide to hexachlorocyclopentadiene being about 1.5 and 2, to form a reaction product thereof; said reacting step being further characterized in that an admixture of the hexachlorocyclopentadiene and the antimony compound is first formed, the sulfur trioxide is added to said admixture to form the reaction mixture, the reaction temperature is maintained below 105°C. during addition of the sulfur trioxide, and the reaction mixture is reacted until it turns to a black color;
   b. hydrolyzing the reaction product from step (a) in at least about 5 parts by weight of an aqueous solution containing dissolved caustic alkali and having a pH of at least 9, per part by weight of reaction mixture, said hydrolysis being carried out at a temperature between about 85°C. and about 115°C. for at least about 30 minutes until all solids have gone into solution;
   c. acidifying the hydrolysis mixture from step (b) with a mineral acid to pH 5–6;
   d. digesting the acidified hydrolysis mixture at pH 5–6 at a temperature between about 85°C. and about 105°C. for at least 1 hour, until the decachlorooctahydro-1,3,4-metheno-2H-cyclobuta(c,d)-pentalen-2-one is completely precipitated as a crystalline product; and
   e. recovering the crystalline product from the digestion mixture.

2. The process of claim 1 wherein hydrolysis step (b) is carried out at a temperature between about 85°C. and about 115°C. for 60 to 120 minutes.

3. The process of claim 1 wherein the mineral acid used in acifidying step (c) is sulfuric acid and the hydrolysis mixture is acidified to pH 5.4–5.6.

4. The process of claim 1 wherein digesting step (d) is carried out at pH 5.4–5.6 for 1–4 hours.

5. The process of claim 1 where the crystalline product is recovered from the digestion mixture in step (e) by filtration, washing with water, and drying.

6. A process for producing decachlorooctahydro-1,3,4-metheno-2H-cyclobuta(c,d)-pentalen-2-one in at least 95% yield, which comprises:
   a. reacting hexachlorocyclopentadiene and sulfur trioxide at a temperature between about 95°C. and about 120°C., at a pressure of between 50 p.s.i.g. and 300 p.s.i.g., in the presence of a catalytic quantity of an antimony compound selected from the group consisting of trivalent and pentavalent antimony halides, oxides and oxy acids, the mole ratio of sulfur trioxide to hexachlorocyclopentadiene being between about 1.5 and 2, to form a reaction product thereof; said reacting step being further characterized in that an admixture of the hexachlorocyclopentadiene and the antimony compound is first formed, the sulfur trioxide is added to said admixture to form the reaction mixture, the reaction temperature is maintained below 105°C. during addition of the sulfur trioxide, and the reaction mixture is reacted until it turns to a black color;
   b. hydrolyzing the reaction product from step (a) in at least about 5 parts by weight of an aqueous solution containing dissolved caustic alkali and having a pH of at least 9, per part by weight of reaction mixture, said hydrolysis being carried out at a temperature between about 85°C. and about 115°C. for 60 to 120 minutes until all solids have gone into solution;
   c. acidifying the hydrolysis mixture from step (b) with sulfuric acid to pH 5.4–5.6;
   d. digesting the acidified hydrolysis mixture at pH 5.4–5.6, at a temperature between about 85°C. and about 105°C. for 1–4 hours, until the decachlorooctahydro-1,3,4-metheno-2H-cyclobuta(c,d)-pentalen-2-one is completely precipitated as a crystalline product; and
   e. recovering the crystalline product from the digestion mixture.

7. The process of claim 6 wherein the hexachloropentadiene and sulfur trioxide are reacted in step (a) at a temperature of 95°–105°C., at a pressure of 85–115 p.s.i.g. for about 1-2 hours.

8. The process of claim 6 wherein the hydrolysis step (b) is carried out at a temperature of about 90°–96°C. in aqueous sodium hydroxide solution having a pH of about 9.5 to 10.5.

9. The process of claim 6 wherein the crystalline product is recovered from the digestion mixture in step (e) by filtration, washing with water, and drying at a temperature of 93°–94°C.

10. A process for producing decachlorooctahydro-1,3,4-metheno-2H-cyclobuta(c,d)-pentalen-2-one in at least 99% yield, which comprises:
   a. reacting hexachlorocyclopentadiene and sulfur trioxide at a temperature between about 95°C. and about 105°C., at a pressure of between 85 p.s.i.g. and 115 p.s.i.g., for about 1–2 hours in the presence of a catalytic quantity of an antimony compound selected from the group consisting of trivalent and pentavalent antimony halides, the mol ratio of sulfur trioxide to hexachlorocyclopentadiene being between about 1.5 and 2, to form a reaction product thereof; said reacting step being further characterized in that an admixture of the hexachlorocyclopentadiene and the antimony compound is first formed, the sulfur trioxide is added to said admixture to form the reaction mixture, the reaction temperature is maintained below 105°C. during addition of the sulfur trioxide, and the reaction mixture is reacted until it turns to a black color;
   b. hydrolyzing the reaction product from step (a) in at least about 5 parts by weight of an aqueous solution containing dissolved caustic alkali and having a pH of about 9.5 to 10.5, per part by weight of reaction mixture, said hydrolysis being carried out at a temperature of about 90°–96°C. for 60 to 120 minutes until all solids have gone into solution;
   c. acidifying the hydrolysis mixture from step (b) with sulfuric acid to pH 5.4–5.6;

d. digesting the acidified hydrolysis mixture at pH 5.4–5.6, at a temperature between about 85°C. and about 105°C. for 1–4 hours, until the decachlorooctahydro-1,3,4-metheno-2H-cyclobuta(c,d)-pentalen-2-one is completely precipitated as a crystalline product; and e. recovering the crystalline product from the digestion mixture.

* * * * *